(12) United States Patent
Feer et al.

(10) Patent No.: US 9,486,145 B2
(45) Date of Patent: Nov. 8, 2016

(54) MULTIFUNCTION FEEDING TUBE

(75) Inventors: David L. Feer, Brookline, MA (US); Daniel A. Silber, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1006 days.

(21) Appl. No.: 13/581,656

(22) PCT Filed: Feb. 2, 2011

(86) PCT No.: PCT/IB2011/050454
§ 371 (c)(1),
(2), (4) Date: Aug. 29, 2012

(87) PCT Pub. No.: WO2011/107894
PCT Pub. Date: Sep. 9, 2011

(65) Prior Publication Data
US 2012/0323089 A1    Dec. 20, 2012

Related U.S. Application Data

(60) Provisional application No. 61/310,308, filed on Mar. 4, 2010.

(51) Int. Cl.
*A61B 5/00* (2006.01)
*A61B 5/01* (2006.01)
(Continued)

(52) U.S. Cl.
CPC ............ *A61B 5/01* (2013.01); *A61B 5/0421* (2013.01); *A61B 5/0538* (2013.01);
(Continued)

(58) Field of Classification Search
CPC ............... A61J 5/00–5/0096; A61N 1/0517; A61N 1/0519
See application file for complete search history.

(56) References Cited

U.S. PATENT DOCUMENTS

| | | | | |
|---|---|---|---|---|
| 4,088,138 A | * | 5/1978 | Diack et al. | 607/6 |
| 4,444,195 A | * | 4/1984 | Gold | A61N 1/056 600/374 |
| 5,016,646 A | * | 5/1991 | Gotthardt | A61N 1/056 607/122 |

(Continued)

FOREIGN PATENT DOCUMENTS

| | | |
|---|---|---|
| EP | 0092451 A1 | 10/1983 |
| EP | 0992216 A1 | 4/2000 |

(Continued)

OTHER PUBLICATIONS

CONMED Patient Care; "ECOM Endotracheal Cardiac Output Monitor"; 2 pages http://www.conmed.com/products_ECOM.php downloaded Aug. 6, 2012.

*Primary Examiner* — Scott Getzow

(57) ABSTRACT

A medical device comprises: a feeding tube (70) including a feeding lumen (80) with an opening (152) at a distal end of the feeding tube and an electrical lumen (84) having access openings (120) spaced apart along the feeding tube; a set of insulated electrical conductors (82) disposed in the electrical lumen, the set of insulated electrical conductors having electrically exposed portions (132, 132a, 132b) proximate to the access openings; and electrodes (72, 73, 74, 75, 78, 79, 140) comprising electrically conductive material portions (140) disposed in the access openings and electrically contacting the proximate electrically exposed portions of the set of insulated electrical conductors disposed in the electrical lumen. The electrodes include at least one upper or proximal electrode (74, 75, 78, 79) disposed above an expected patient heart electrical centerline (CL) and at least one lower or distal electrode (72, 73) disposed below the expected patient heart electrical centerline.

25 Claims, 9 Drawing Sheets

(51) Int. Cl.
*A61B 5/042* (2006.01)
*A61B 5/087* (2006.01)
*A61J 15/00* (2006.01)
*A61B 5/03* (2006.01)
*A61B 5/053* (2006.01)
*A61B 5/08* (2006.01)

(52) U.S. Cl.
CPC .......... *A61B 5/0878* (2013.01); *A61B 5/6846* (2013.01); *A61J 15/0003* (2013.01); *A61J 15/0073* (2013.01); *A61J 15/0084* (2015.05); *A61B 5/037* (2013.01); *A61B 5/0422* (2013.01); *A61B 5/053* (2013.01); *A61B 5/0816* (2013.01); *A61B 2562/0209* (2013.01); *A61B 2562/0271* (2013.01); *A61B 2562/043* (2013.01); *Y10T 29/49117* (2015.01)

(56) References Cited

U.S. PATENT DOCUMENTS

| | | | |
|---|---|---|---|
| 5,199,433 A * | 4/1993 | Metzger et al. | 600/380 |
| 5,782,774 A | 7/1998 | Shmulewitz | |
| 5,791,349 A | 8/1998 | Shmulewitz | |
| 6,095,987 A | 8/2000 | Shmulewitz et al. | |
| 6,292,689 B1 | 9/2001 | Wallace et al. | |
| 8,756,806 B2 | 6/2014 | O'Dea et al. | |
| 2006/0173449 A1 | 8/2006 | Sharareh et al. | |

FOREIGN PATENT DOCUMENTS

| | | |
|---|---|---|
| GB | 2254253 A | 10/1992 |
| GB | 2397231 A | 7/2004 |
| WO | 9959463 A1 | 11/1999 |
| WO | 2005115234 A1 | 12/2005 |
| WO | 2006015230 A2 | 2/2006 |
| WO | 2008059415 A1 | 5/2008 |
| WO | 2008072150 A1 | 6/2008 |

* cited by examiner

MULTIFUNCTION FEEDING TUBE

CROSS REFERENCE TO RELATED APPLICATIONS

This application claims the benefit of U.S. provisional application Ser. No. 61/310,308 filed Mar. 4, 2010, which is incorporated herein by reference.

The following relates to the medical care arts, neonatal and pediatric care, feeding tubes for neonatal patients or pediatric or adult patients, physiological monitoring arts, and so forth.

A neonatal patient, such as a newborn baby with an identified medical condition, or a prematurely born baby, or so forth, is sometimes fed via feeding tube. In a nasogastric feeding tube arrangement, for example, a feeding tube is inserted into a nasal orifice and is passed down through the esophagus to terminate in the stomach. Feeding tubes are also used for pediatric or adult patients who cannot ingest adequate sustenance due to a medical condition.

Patients undergoing therapy employing a feeding tube are typically also subject to monitoring of one or more physiological parameters such as cardiac cycling (e.g., heart rate and/or ECG), respiration, core body temperature, or so forth. The neonatal or other patient is thus connected with a feeding tube and physiological probes such as electrocardiograph (ECG) electrodes, a thermister or other temperature sensor, or so forth. The feeding tube and the various physiological probes are connected with corresponding monitoring devices (ECG monitor, patient thermometer, or so forth) by wires or cables. The patient is made uncomfortable by these connections, patient movement is restricted by the wires or cables, and the various wires and cables present physical obstacles for physicians, nurses, or other attending medical personnel. In the case of a neonatal patient, adhesion of skin electrodes can also be problematic due to poor skin development and the humidity and temperature controlled incubator environment.

During insertion of a new feeding tube, care must be taken to ensure that the feeding tube follows the esophageal path to the stomach (rather than the bronchial path into the lungs), and to ensure that the distal end of the feeding tube is properly positioned (typically in the stomach, rather than in the esophagus or lower down in the stomach). Incorrect positioning of the feeding tube can result in aspiration of feeding material into the lungs or other medical complications. Problematically, existing feeding tubes typically do not provide positive positional feedback during insertion.

The feeding tube is a disposable device, that is, it is generally not reused for different patients. In the case of a prematurely born baby, undersized baby, or other neonatal patient, the feeding tube may need to be replaced frequently due to typically rapid neonatal growth rate. As a disposable item, it is advantageous for the feeding tube to be of low manufacturing cost. The feeding tube also should remain reliable under exposure to the esophageal and stomach environment, which is highly acidic and includes corrosive digestive fluids. In practice, feeding tubes are typically simple hollow tubular elements of silicone, polyurethane, or another robust material.

The present application provides new and improved feeding tubes, and methods of manufacturing and using same, which overcome the above-referenced problems and others.

In accordance with one aspect, a device comprises: a feeding tube including a feeding lumen with an opening at a distal end of the feeding tube and an electrical lumen having access openings spaced apart along the feeding tube; a set of insulated electrical conductors disposed in the electrical lumen, the set of insulated electrical conductors having electrically exposed portions proximate to the access openings; and electrodes comprising electrically conductive material portions disposed in the access openings and electrically contacting the proximate electrically exposed portions of the set of insulated electrical conductors disposed in the electrical lumen.

In accordance with another aspect, a method of constructing a device is disclosed, the method comprising: forming a feeding tube including a feeding lumen and an electrical lumen parallel with at least a portion of the feeding lumen and having access openings spaced apart along the feeding tube; inserting a set of insulated electrical conductors into the electrical lumen of the feeding tube, the set of insulated electrical conductors having electrically exposed portions that are proximate to the access openings after the inserting; and after the inserting, forming electrodes by a process including injecting electrically conductive material portions into the access openings of the electrical lumen to electrically contact the proximate electrically exposed portions of the set of insulated electrical conductors disposed in the electrical lumen.

In accordance with another aspect, a device is disclosed which is constructed by the method of the immediately preceding paragraph.

In accordance with another aspect, a device comprises: a feeding tube including a feeding lumen with an opening at a distal end of the feeding tube and an electrical lumen; a set of insulated electrical conductors disposed in the electrical lumen; electrodes disposed along the feeding tube and electrically contacting the set of insulated electrical conductors, the electrodes including a set of upper or proximal electrodes and a set of lower or distal electrodes; and a switch configured to operatively connect one electrode of the set of upper or proximal electrodes and one electrode of the set of lower or distal electrodes to an electrocardiograph (ECG) instrument.

One advantage resides in a reduced number of wires or cables connected with the patient.

Another advantage resides in more accurate physiological monitoring.

Another advantage resides in providing a feeding tube with one or more integral physiological monitoring sensors.

Another advantage resides in reduced manufacturing cost for a feeding tube with one or more integral physiological monitoring sensors.

Another advantage resides providing increased robustness for a feeding tube with one or more integral physiological monitoring sensors.

Still further advantages of the present invention will be appreciated to those of ordinary skill in the art upon reading and understanding the following detailed description.

Figure 6:
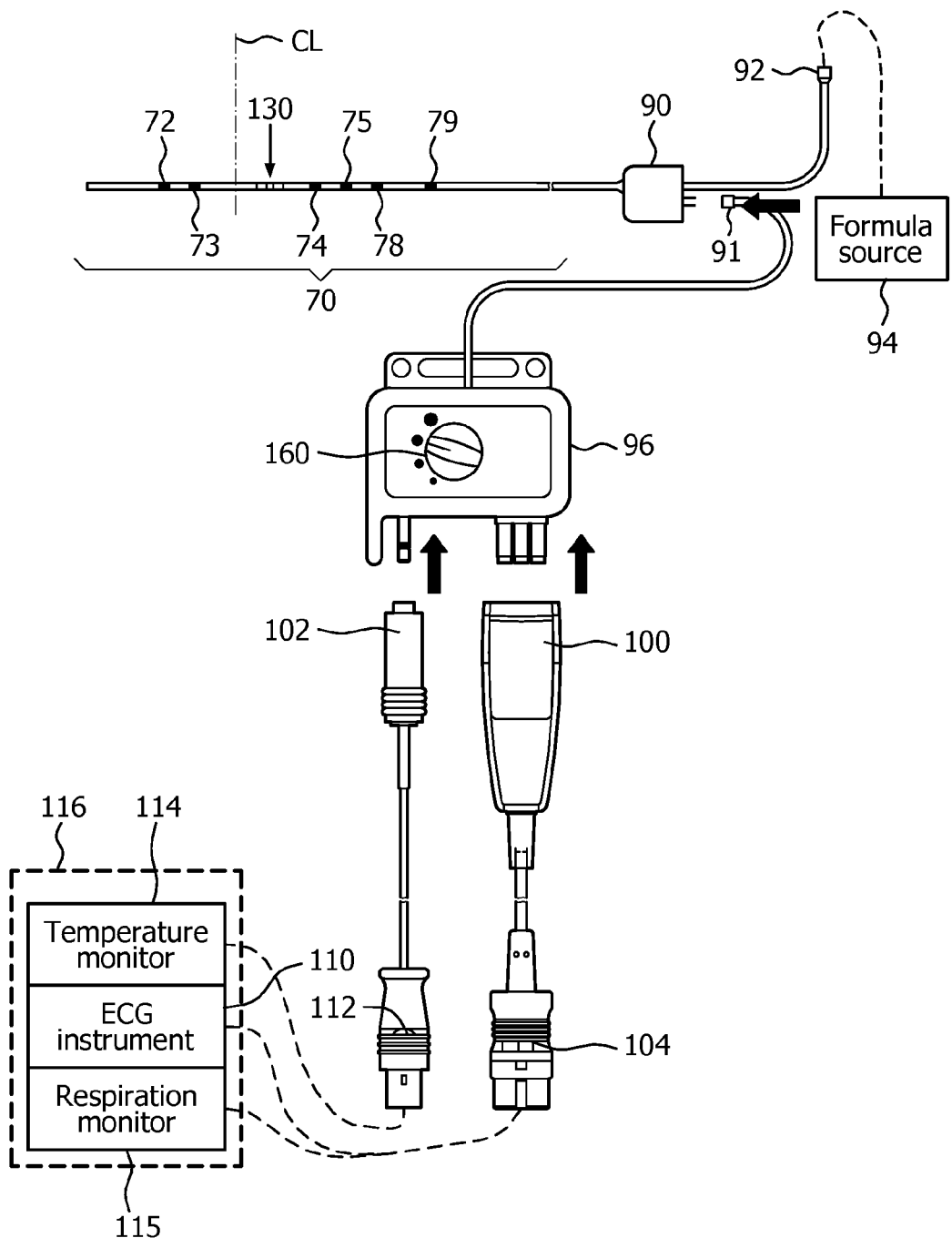

FIG. 6 diagrammatically depicts a medical patient monitoring system including a medical device comprising a multifunction feeding tube.

Figure 7:
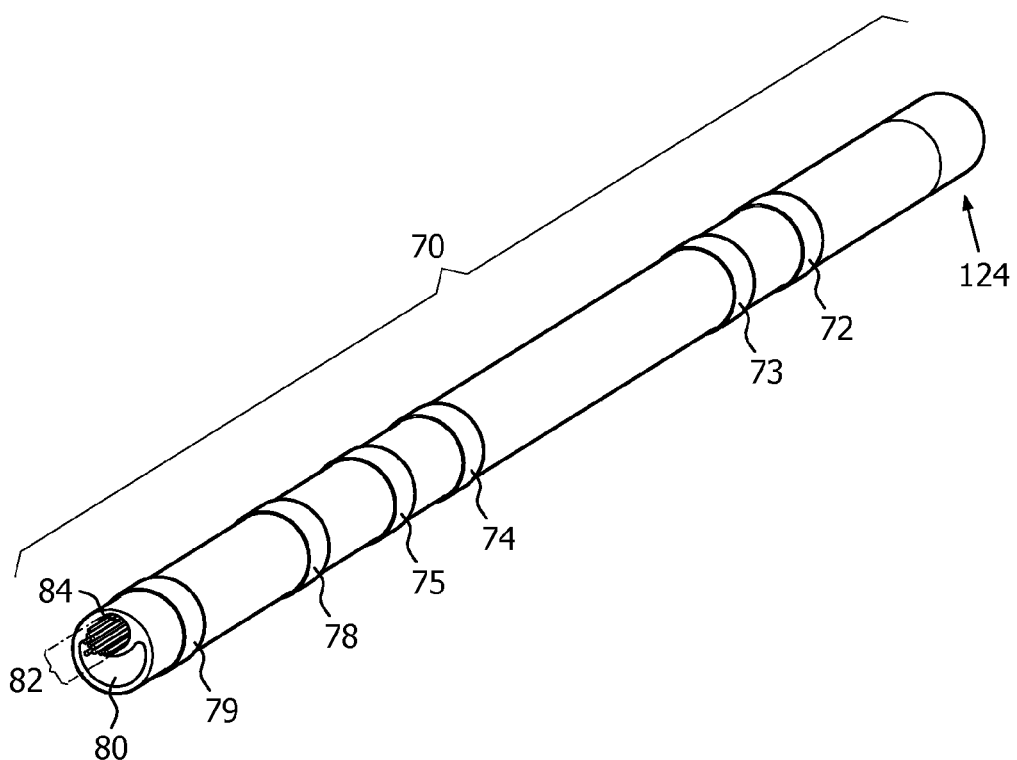

FIG. 7 shows an enlarged perspective view of the multifunction feeding tube of FIG. 6.

Figure 8:
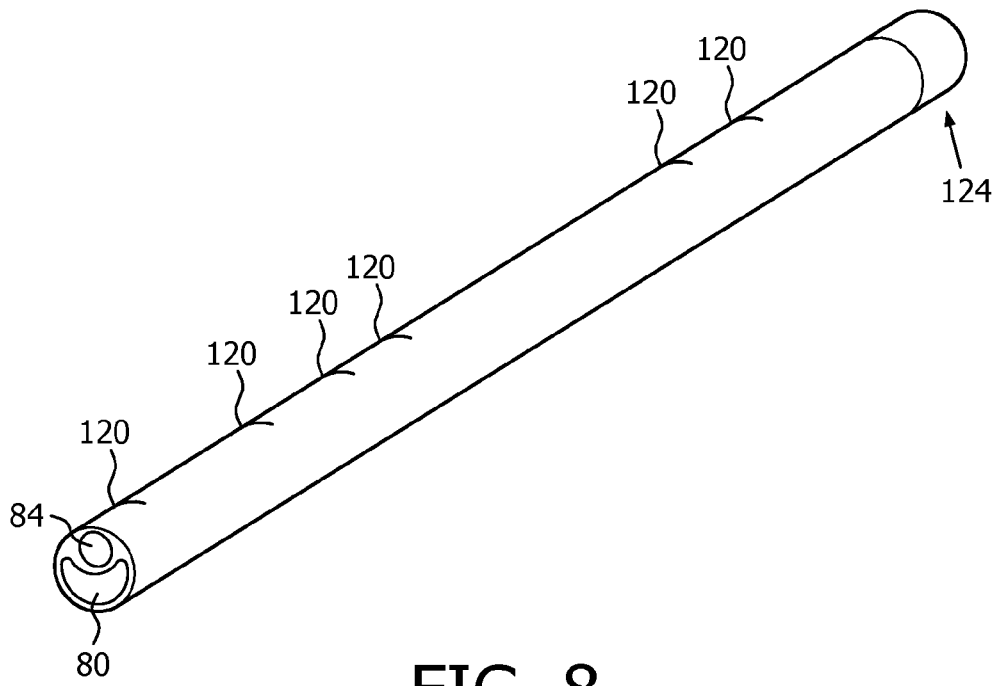

FIG. 8 shows an enlarged perspective view of the multifunction feeding tube extrusion including access openings formed after the extrusion used in fabricating the multifunction feeding tube of FIGS. 6 and 7.

Figure 9B:
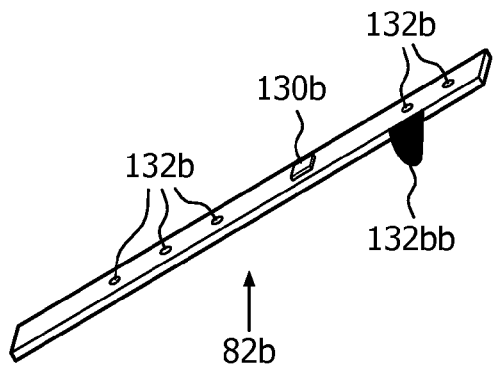
Figure 9:
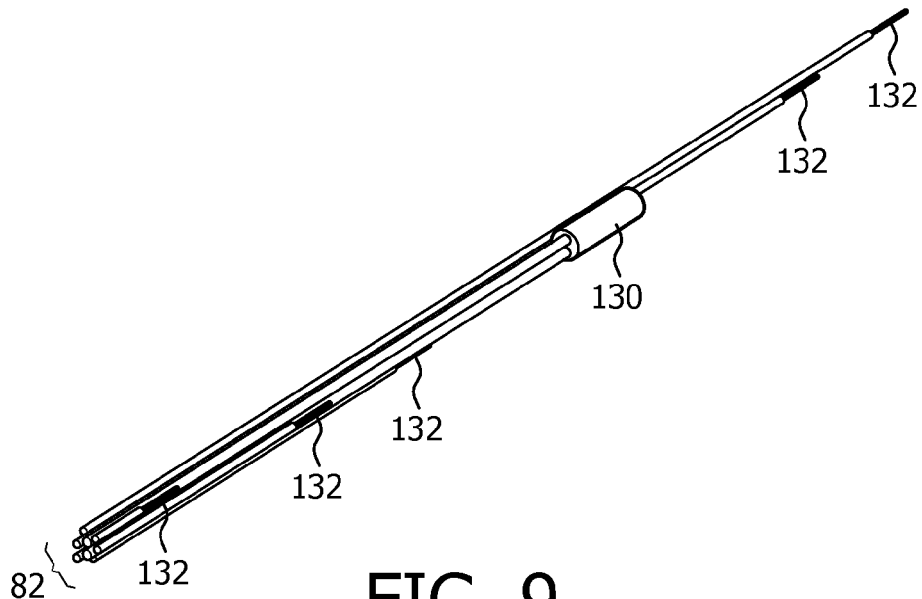
Figure 9A:
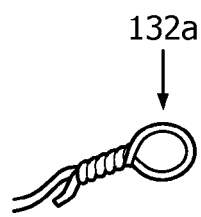

FIGS. 9, 9A, and 9B show various suitable embodiments or aspects of the electrical assembly of the multifunction feeding tube of FIGS. 6 and 7 prior to insertion of the electrical assembly into the electrical lumen of the feeding tube extrusion.

Figure 10:
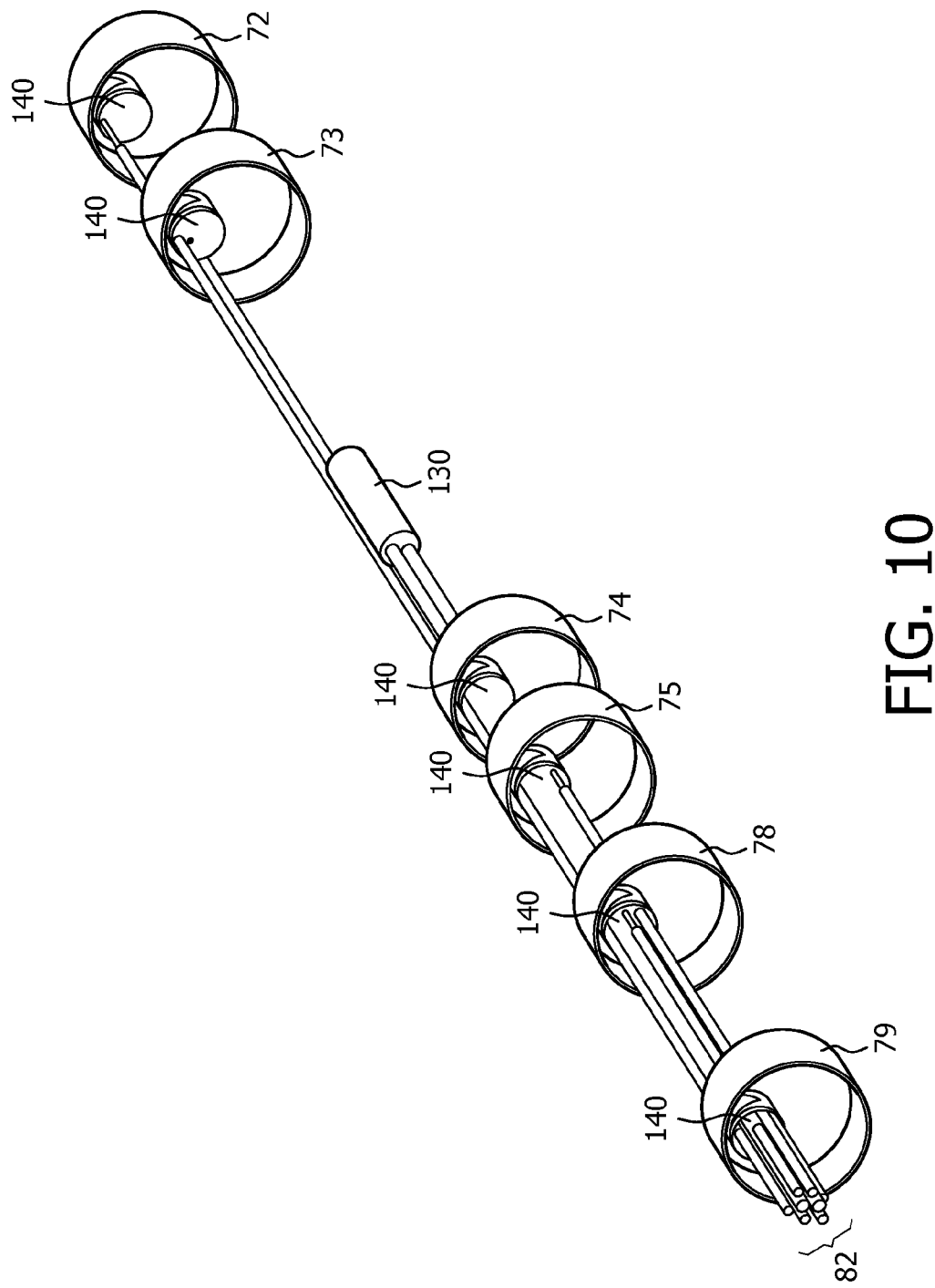

FIG. 10 shows the multifunction feeding tube of FIGS. 6 and 7 with the extrusion removed to reveal the temperature sensor and electrode connections.

Figure 11:
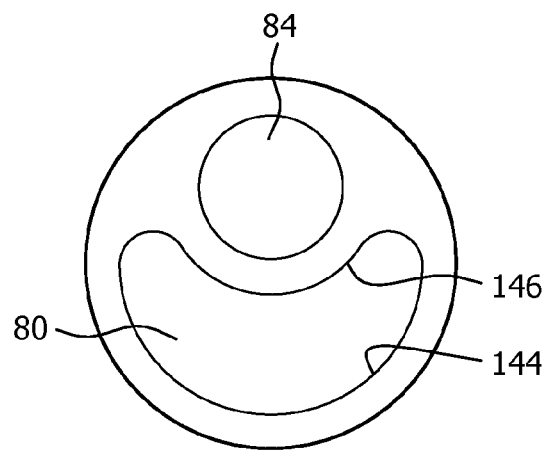

FIG. 11 shows a cross section of the feeding tube extrusion of FIG. 8 revealing the feeding lumen and electrical lumen.

Figure 12:
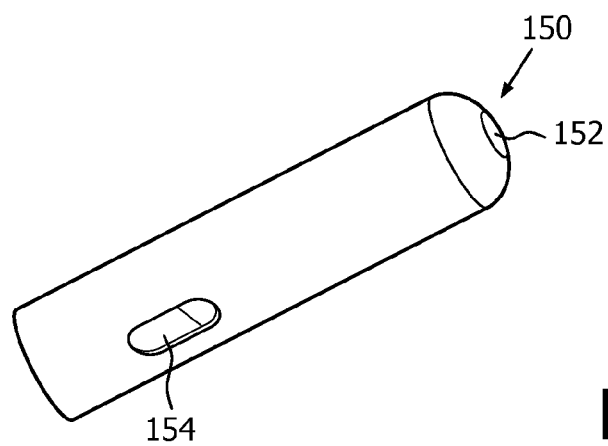
Figure 13:
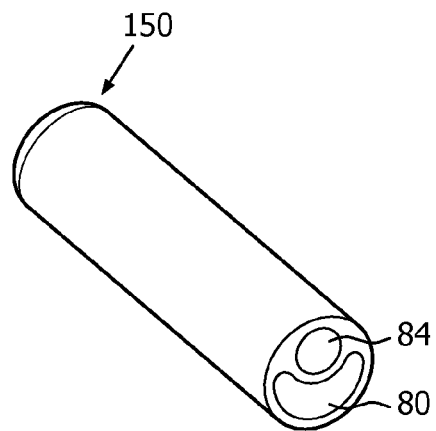

FIGS. 12-13 show perspective views of one suitable embodiment of the distal tip of the multifunction feeding tube of FIGS. 6 and 7.

Figure 14:
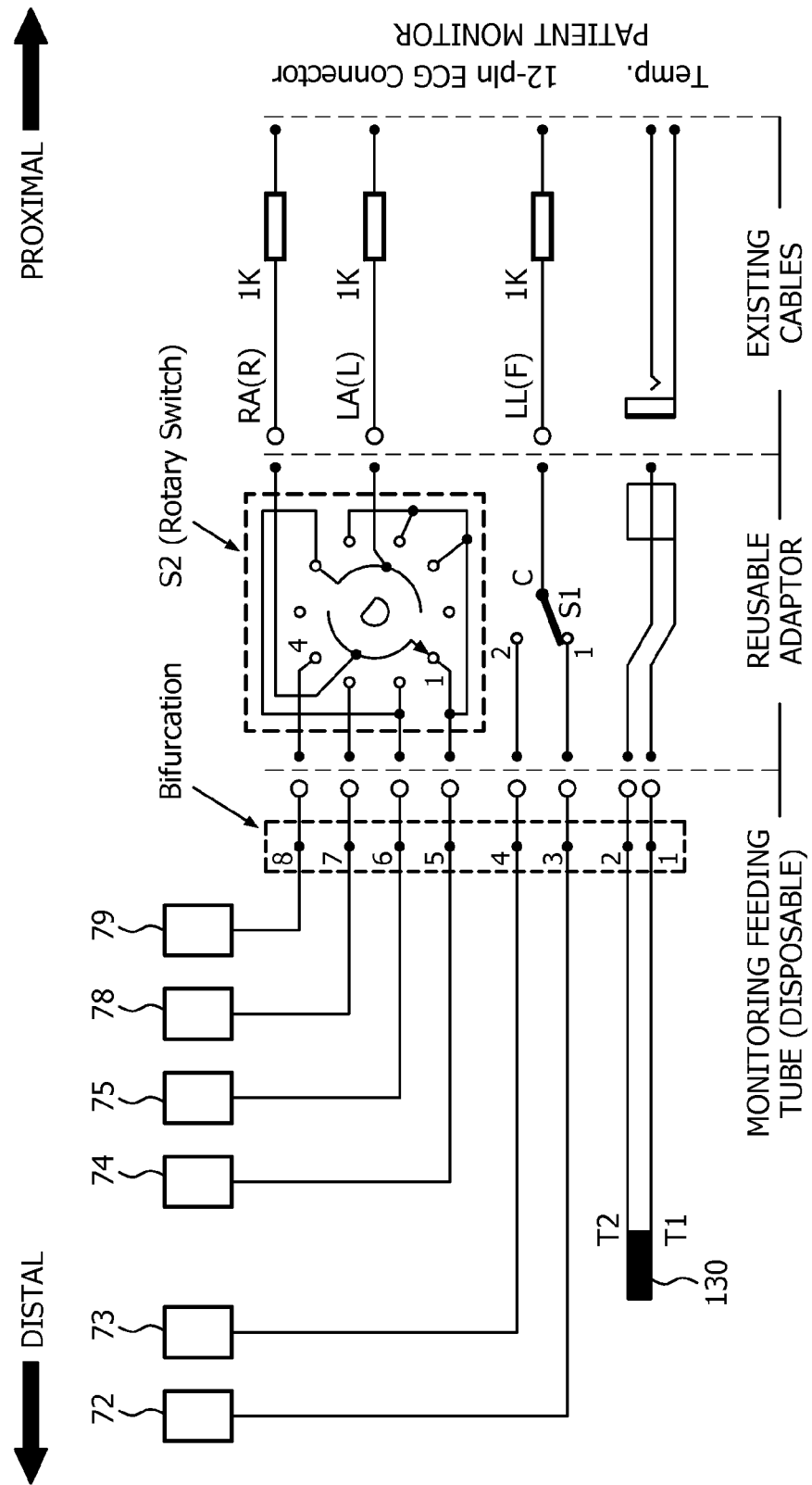

FIG. 14 diagrammatically shows an electrical schematic of a medical device comprising the multifunction feeding tube of FIGS. 6-13 connected to provide electrocardiography capability with selectable ECG electrodes.

Figure 1:
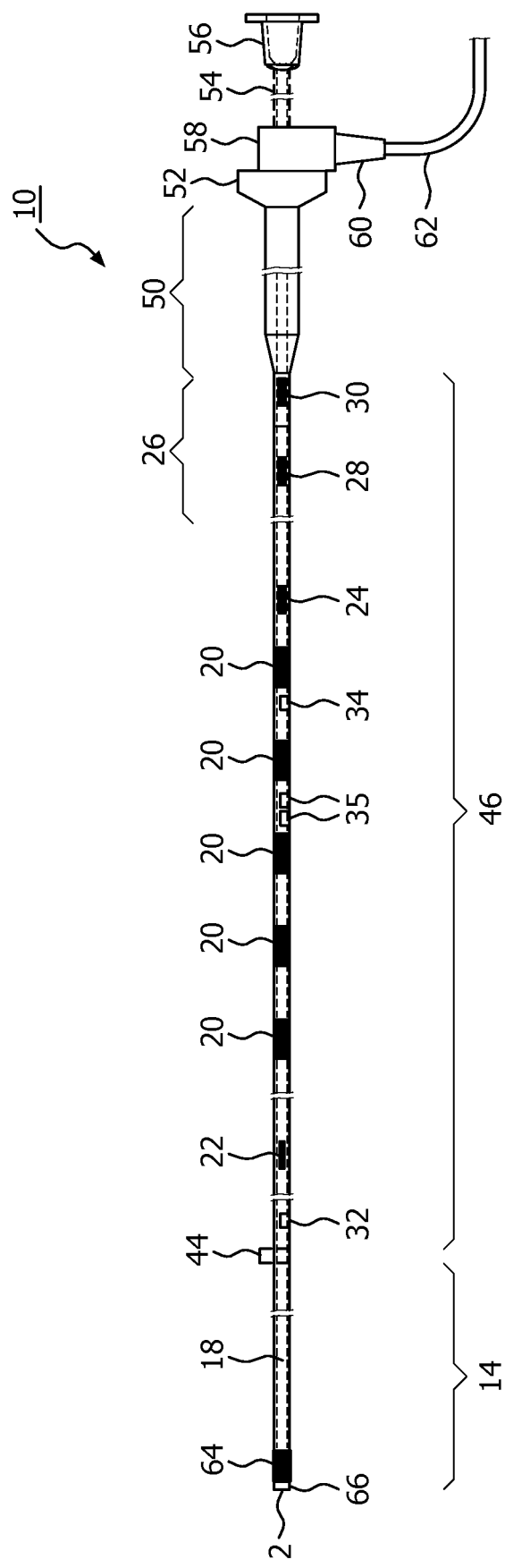
FIG. 1 depicts a neonatal feeding tube with instrumentation, in accordance with the present application.

With reference to FIG. 1, a neonatal feeding tube 10 is depicted. In one embodiment, the tube 10 is an instrumented disposable feeding tube for newborn infants (neonates) who have not yet developed their sucking capabilities, or who are unable to feed normally for some other reason. The tube 10 is a 5 French tube, or 1.67 mm in diameter, in one embodiment. Appropriate scaling can be performed for larger or smaller tubes. It is also to be understood that although neonatal feeding tubes are described as illustrative examples herein, more generally the disclosed feeding tube embodiments and disclosed aspects thereof are readily applied to feeding tubes for adult patients, veterinary subjects (e.g., dogs or cats undergoing veterinary care), or so forth. For convenience, the tube 10 is shown segmented, though its actual size is approximately 300 mm in length, for example.

Figure 2:
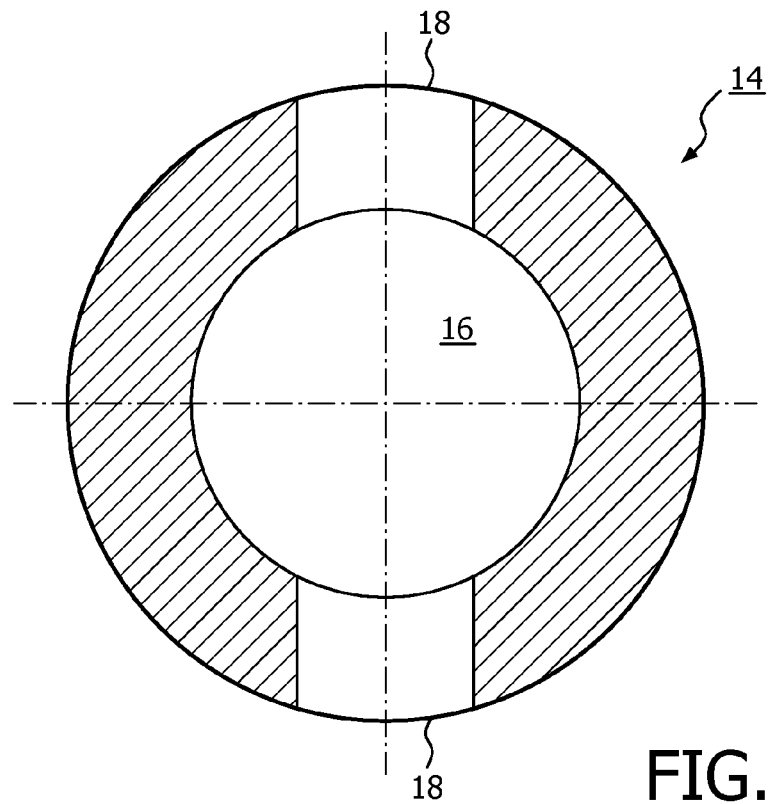
FIG. 2 is a cross sectional view of the feeding tube of FIG. 1 through a distal portion.

The neonates are fed formula or breast milk through the tube 10. The tube 10 is typically inserted into the nose (that is, a nasogastric feeding tube arrangement) or mouth and advanced into and through the esophagus, and into the stomach. The tube 10 has a tip 12 at the distal end of the tube that is typically disposed in an upper region of the stomach when the feeding tube 10 is properly inserted. FIG. 2 depicts a cross sectional view of the distal portion 14. A hole 16 in the tip 12 permits food, such as infant formula or breast milk, to exit the tube. One or more additional holes 18, offset from the tip 12, allow feeding to exit in the event that the end hole 16 becomes clogged or otherwise blocked. The tip 12 and cross holes 18 are preferably located in the subject's stomach in one embodiment. The distal portion 14 is suitably molded of a soft, biocompatible material, such as (in one embodiment) silicone rubber.

Figure 3:
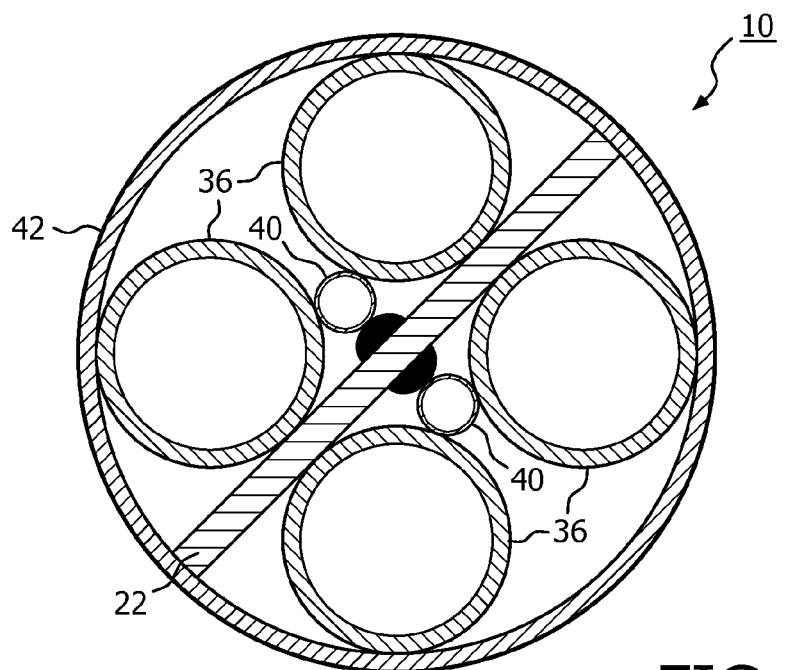
FIG. 3 is a cross sectional view of the feeding tube of FIG. 1 through a thermistor.

The feeding tube 10 also includes electrodes 20. The electrodes 20 are on an outside of the feeding tube and, when inserted, make contact with the subject's esophagus. Insulated leads extend proximally from each electrode, either inside the feeding tube 10 or the outer wall of the feeding tube. A temperature sensor, which in the illustrated example is a thermister 22, is disposed inside the tube for taking temperature measurements and, in one embodiment, lies distal to the electrodes 20. FIG. 3 shows a cross section of the tube 10 including the thermistor 22 in cross-section. Other temperature sensors can be used in place of the illustrated thermister 22, such as a thermocouple, a thermodiode, or so forth.

The thermistor 22 is assembled to a pair of wires, at least one insulated. In one embodiment, the thermistor 22 is calibrated to operate with a specific patient monitor or series of monitors. The calibration is optionally checked prior to insertion of the feeding tube 10 into the patient, for example by measuring resistance and compared to a specification. In an optional calibration operation, resistance is increased as appropriate until the thermistor resistance meets the specification, so as to bring the thermistor into compliance with specified standards for accuracy. The illustrative thermistor 22 may be one piece of semiconductor material or it may be two or more segments connected in parallel, with a small gap between each segment. This allows the assembly to flex in two directions and to twist, even if the length is several multiples of the tube diameter. The overall resistance of the thermistor is proportional to its thickness and inversely proportional to the area. Because the width of the thermistor and thickness of the thermistor are constrained by the size of the tube 10, the effective length of the thermistor assembly is selected based on the electrical requirements of the monitoring system. This method of construction also minimizes difficulty and discomfort during insertion, removal, and use. It is also more flexible and more resistant to breakage during manufacture, insertion, and use. In one embodiment, the thermistor 22 has a resistance of approximately 2250Ω at 25° C. and approximately 1360Ω at 37° C.

In a single-thermistor embodiment, when the tube is inserted the thermistor 22 is suitably located in the esophagus so as to accurately measure core temperature, rather than the stomach or pharynx, where readings would be less accurate. Placement in the stomach can be problematic due to the corrosive effects of gastric fluids and the inaccuracy that might be caused by air or food in the stomach.

Proximal to the electrodes 20 is a nasopharyngeal section 26 of the feeding tube 10. The nasopharyngeal section 26, as the name indicates, lies inside the pharynx and nose when inserted. This section is suitably smooth and small in diameter to reduce irritation to the subject and interference with air flow during breathing. In an alternate embodiment, it has a non-circular shape and/or concave flutes to reduce the possibility of complete blockage of a nare. In some embodiments, a hypopharynx thermistor 28 and an oropharynx thermistor 30 are included in the nasopharyngeal section 26. The thermistors 28, 30 are used to measure respiration flow, in addition the distal or caudal thermistor provides a core temperature measurement. The respiration flow is measured as a relative temperature change between the oropharynx thermistor 30 and the hypopharynx thermistor 28. An array of these thermistor pairs may be provided to accommodate various patient sizes.

A pressure differential ΔP is measured by a pressure gradient between a sub-diaphragmatic (or caudal) port 32 and a supra-diaphragmatic (or cephalic) port 34. ΔP represents the respiration effort of the subject. Flow can be measured separately (with thermistors 28 and 30), as an airway obstruction may produce increased effort but no ΔP. Respiration flow and respiration effort are measured separately and can differ. For example, in the case of an airway obstruction, effort will increase but flow will decrease. The measured flow can be cross-checked against ΔP for accuracy, and can signal an alarm if the two do not coincide.

In the illustrative embodiment of FIG. 1, proximal to the supra-diaphragmatic pressure port 34 are two fiber optic windows 35. The fiber optic windows 35 are polished ends of many fiber optic strands. At the proximal end of the feeding tube the fiber optic strands separate into a source fiber (run from a light source, not shown) and a return fiber. Both fiber bundles run down the tube 10 to the fiber optic windows 35. One fiber optic bundle terminates in the esophagus and another at the distal tip of the feeding tube. The distal fiber bundle does not need to be separated into a sending and receiving bundle as it is used only to send light down which would emanate from the small patient due to the thin membranes and relatively translucent nature of the skin. This tip light is used for placement verification by energizing the fibers from an external light source and in a darkened room and visualizing the location of the light emanating from the patient's abdomen (if properly placed) or thorax (if not properly placed). The pulse of the subject is measured by reflectance photo-plethysmogram through the fiber optic window using traditional reflectance pulse oximetry techniques. Core $SpO_2$ is also measured at the fiber optic window 35. The supra-diaphragmatic port 34 serves as a flush location to clean the fiber optic window 35 as needed.

Figure 4:
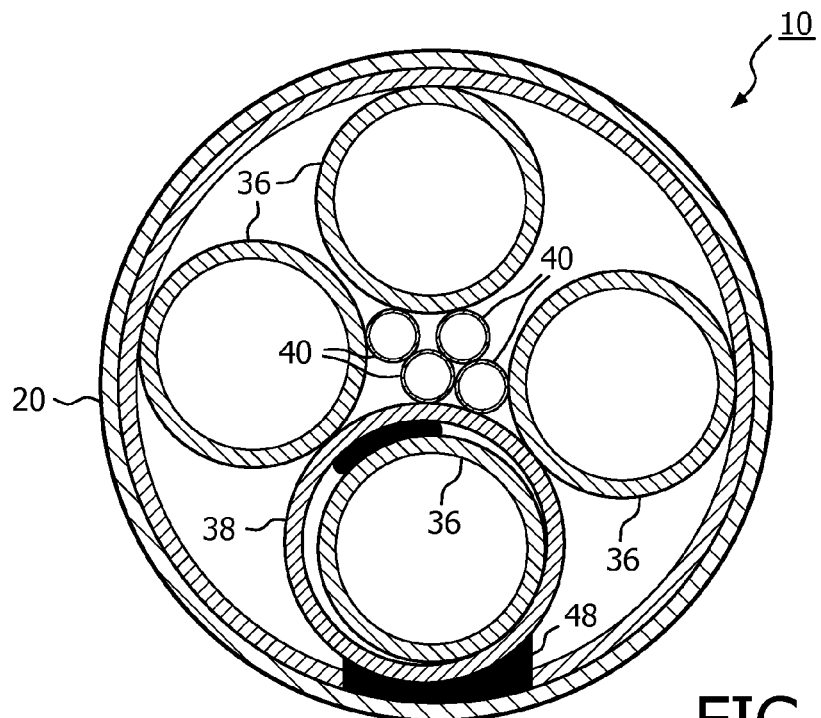
FIG. 4 is a cross sectional view of the feeding tube of FIG. 1 through an electrode.
Figure 5:
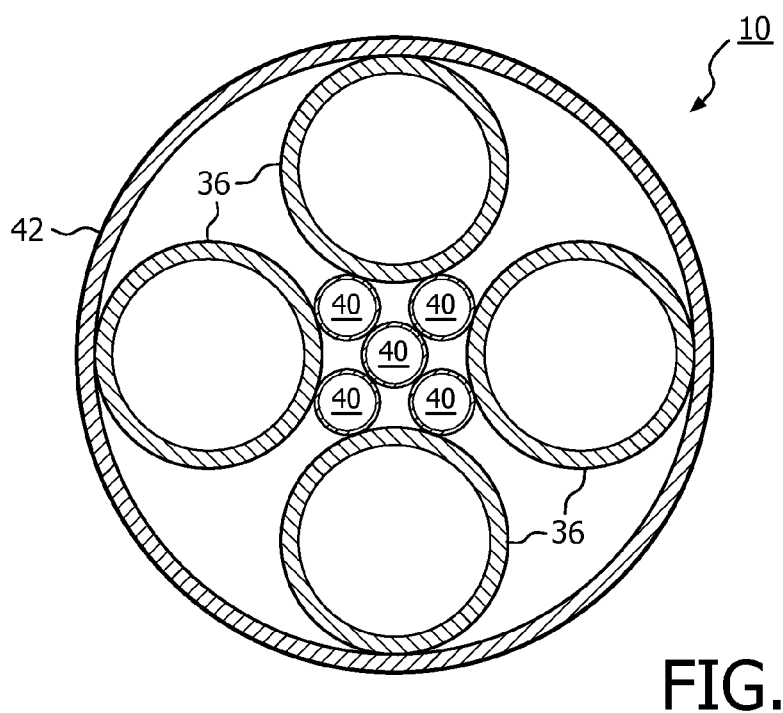
FIG. 5 is a cross sectional view of the feeding tube of FIG. 1 through a proximal portion.

With reference now to FIG. 4, and continuing reference to FIGS. 1-3, an illustrative method of manufacture is disclosed. In one embodiment, there are four feeding lumens 36. In a three-electrode embodiment, three of the four lumens 36 carry a contact for an electrode 20, and one lumen 36 does not. In a four-electrode embodiment, each of the four lumens 36 can carry a contact for an electrode 20. In a five-electrode embodiment, three of the four lumens 36 carry one contact while the fourth lumen 36 carries two contacts. Fewer or additional electrodes 20 can be positioned appropriately following the same pattern. The lumens 36 are cut to length. At the appropriate location for each electrode 20, an un-insulated end of a wire is secured. In one embodiment, the wire is electrically and mechanically connected to a metal fitting 38 by soldering, welding, bonding with a conductive adhesive, crimping, or the like. The fitting 38 is then attached to the lumen 36 in the appropriate position, either by swaging, crimping, adhesive, or the like.

The lumen 36 and the thermistors 22, 24, 28, 30 are placed together with the thermistors 22, 24, 28, 30 and wires 40 in the center of the lumens 36, as depicted in FIG. 3. The distal portion 14 is brought together with the lumens 36 and thermistors 22, 24, 28, 30, held in place, and a jacket 42 is applied by extrusion, heat-shrinking, tape wrapping, or the like. The lumens 36 may reshape somewhat during this process, but this is inconsequential to the operation of the feeding tube 10. The wires 40 are preferably located in the center of the tube 10 for maximum flexibility. If additional bond strength is needed, a mechanical strength member (wire or fiber) can be added to the distal portion 14 and secured to the wires 40. A gap 44 between the distal portion 14 and a proximal portion 46 inside the jacket 42 serves as a blending area for flow from the multiple lumen 36 to blend and enter the distal part 14 and flow out the holes 16, 18 into the subject's stomach. Next, the electrodes 20 are added.

With reference to FIG. 4, the jacket 42 is removed in the area of the electrode 20. A conductive transition 48 such as a conductive adhesive, spring-like device, or the like is placed in the resulting removed area. An electrode 20, in the form of a short thin-wall cylinder, is placed over each conductive transition 48 and is then swaged to lock it in place. The proximal and distal edges are then bent into the jacket 42 to provide a smooth surface to reduce risk of injury to the patient.

An outside portion 50 of the tube 10 lies outside of the subject when the feeding tube 10 is inserted. The outside portion 50 may have a larger cross section. The wires 40 that run from the components within the tube 10 terminate in a tube-side connector 52. A feeding lumen extension 54 may pass through the approximate center of the tube-side connector 52 and terminates in an oral style fitting 56 that permits baby formula or breast milk to be injected by syringe, drip, pump, or other means. In one embodiment, the fitting 56 is marked or physically differentiated to distinguish it from ports meant for vascular injection.

Mating with the tube-side connector 52 is a cable-side connector 58. In one embodiment, the cable-side connector 58 has a slot (not shown) that allows the cable-side connector 58 to be connected or disconnected without disturbing the feeding tube lumen extension 54. After passing through a flex relief section 60, external electrical wires 62 continue to a monitor. The external wires 62 may be fitted with an adapter that allows interface to various makes or models of patient monitors.

The outside portion 50, tube-side connector 52, feeding connector 56 and lumen extension 54 are secured using conventional insert molding, over-molding, and bonding techniques. An over-molded or assembled tube-side connector 52 mates with the cable-side connector 58 on the external wiring 62. The multiple feeding lumens 36 transition into a single lumen in the outside portion 50. The lumen extension 54 continues through openings in the connector parts 52, 58. In the lumen extension 54 there are no wires involved, and it is relatively transparent, which facilitates visual confirmation of flow. The lumen extension 54 is also flexible. If a caregiver needs to interrupt flow by pinching off the lumen, it should be done at the lumen extension 54. Once assembled, the feeding tube 10 is ready to be sterilized and packaged.

Typically, three electrodes are employed for ECG readings. For small neonates, the distal three electrodes 20 are suitably used. For medium neonates, the middle three electrodes 20 are suitably used. For larger neonates, the proximal three electrodes 20 are suitably used. In one embodiment, the electrodes are selected manually based on the size of the neonate, and the judgment of the caregiver. The setting can be selected by the caregiver by temporarily disconnecting the connector, rotating the cable-side part 58 relative to the connector 52, and then re-connecting, thereby changing which internal contacts are used. In another embodiment, the electrodes are selected by the monitor. Once the tube is inserted, all electrodes 20 send signals to the monitor. The monitor displays multiple wave-forms, and the operator selects the clearest display. In other embodiments, all signals are recorded or the monitor automatically chooses the best electrodes.

In some embodiments, respiration rate is determined by injecting a low-voltage electrical signal into the patient via a pair of spaced ECG electrodes. The electrical impedance of the connection varies during the act of respiration, so the rate and depth of respiration can be estimated based on the electrical impedance variation. In some embodiments, the respiration rate is derived using electrodes selected from the array of available electrodes.

In an alternate embodiment a U-shaped connector on the monitor side is used so that the feeding tube 10 can be in the center, with mating in the axial direction. The U-shape allows the electrical connection and the feeding connection to be made or disconnected in any sequence, without mutual interference. In another alternate embodiment, a connector is on the side of the feeding tube, with mating in the radial or oblique direction. In another alternate embodiment, the tube 10 has a rectangular (linear) connector rather than a circular or U-shaped connector. In this embodiment, the feeding tube side would have a number of sockets (pins) equal to the number of electrodes, while the cable side would have a number of pins equal to the number of electrodes used by the monitor. The cable could then be plugged in to the feeding tube 10 in a number of locations, thereby selecting which electrodes are operative. In another alternate embodiment, the tube 10 has a connector where the selection of the electrodes is performed by a switching device inside the cable-side connector 58, or the cable 62 itself. In another alternate embodiment, the tube 10 has a connector with a rotating collar or other device which could be locked into place to assure that the connector, after disconnection, can only be re-connected in the selected position. In another alternate embodiment, the tube 10 has a slide or rotary switch on the connector to allow the caregiver to manually select the electrodes with the strongest signal as shown on a monitor display. The foregoing are merely illustrative examples.

Proper insertion of the feeding tube 10 can be problematic in some instances. The tube is to be inserted to a depth that places the tip 12 of the tube 10 in the stomach of the neonate. It is undesirable to insert the tube too far, e.g. into the duodenum, and it is also undesirable to insert the tube not far enough, such that the openings 16, 18 are in the esophagus. With reference again to FIG. 1, a distal electrode 64 on the tip 12 of the tube 10 is optionally included to facilitate placement confirmation. While the distal electrode 64 remains in the esophagus, contact with the wall of the esophagus produces electrical continuity. However, when the distal electrode 64 passes through the esophageal sphincter into the larger opening of the stomach, the electrical continuity decreases or disappears. Because the relative location of the electrode 64 and the openings 18 is established by the detailed design of the device, the location of the openings 18 is thus known to the clinician relative to the beginning of the patient's stomach.

In conjunction with the electrode 64, an optional light source 66 can be used to judge the position of the tip 12 as it is passed down the subject's esophagus. The neonate's chest is relatively thin and translucent. The light source 66, if bright enough, can be seen through the neonate's chest, and the caregiver can visually verify the position of the tip 12. The light source 66 may be illuminated by a lamp outside the proximal end and an optic fiber running the length of the tube 10. It is also contemplated that a fiber optic camera could be located at or fiber optically connected to the tip 12 and used as a traditional endoscope to aid in positioning the tube 10. In some embodiments, the fiber optic device is a permanent part of the tube 10; whereas, in alternative embodiments, the fiber optic device is inserted into a feeding lumen 36 prior to placement in the body and removed after the tube 10 is properly placed, so that the lumen 36 may be used for feeding.

When inserting the tube 10, the tube should follow the esophagus and not veer into the lungs. One way to tell which path is being followed is by a temperature measurement with thermistors at the tip 12. If different temperatures are measured with inhale and exhale respiration, the tip is in an air passage. If the temperature is constant, the tip is in the esophagus. Monitoring pressure at the tip can be used analogously. Pressure can be measured by sealing one of the lumens and adding a pressure port.

Another optional aid in positioning the tube 10 is to include a sensor that measures pH. If the tip 12 is properly in the stomach, the measured pH should be acidic. If the tip 12 is in the lungs, the measured pH will be neutral. If the tip 12 is in the esophagus, the measured pH will be somewhat acidic, depending on reflux, etc.

With reference to FIGS. 6-14, some other feeding tube embodiments are described. Again, these embodiments are described with reference to neonatal application, but the disclosed feeding tube systems are also readily adapted for pediatric or adult patients by suitable size scaling and the like. The illustrative feeding tube system shown in FIGS. 6-14 is a multifunction system that provide both feeding and monitoring, and has aspects disclosed herein that enhance manufacturability, reduce manufacturing cost, enhance feeding tube robustness and reliability, accommodate patient growth, and provide other benefits.

With reference to FIGS. 6 and 7, a medical device includes a feeding tube 70 designed to provide both feeding functionality and additional electrocardiographic (ECG), respiration monitoring, temperature, and optional other monitoring functionality. Toward the latter end, the feeding tube 70 (or, more precisely, a distal end of the feeding tube designed for nasogastric or other insertion into the subject) includes electrode rings 72, 73, 74, 75, 78, 79, a and a temperature sensor 130. Food flows through a feeding lumen 80 of the feeding tube 70. The electrode rings 72, 73, 74, 75, 78, 79, and the temperature sensor 130 are connected with a set of wires 82 disposed in an electrical lumen 84 of the feeding tube 70. At a proximal end of the feeding tube 70 a bifurcation 90 or other coupling element connects a feeding inlet 92 with a formula source 94 or other source of food that is delivered to the feeding inlet and through the feeding lumen 80 into the subject's stomach. The feeding inlet 92 is preferably a standardized connector for this purpose; accordingly, the connection of the formula source 94 with the feeding inlet 92 is shown diagrammatically. At the bifurcation 90, a connector 91 connects the set of wires 82 to an electrical adaptor 96, which adapts the wires of the set of wires 82 from the ECG electrode rings 72, 73, 74, 75, 78, 79 into a standard electrocardiograph (ECG) trunk cable 100. The connector 91 also connects the wires of the set of wires 82 from the temperature sensor 130 to a standard temperature probe cable 102. The ECG trunk cable 100 has a connector 104 for connecting to the electrocardiograph (ECG) instrument 110, while the temperature probe cable 102 has a standardized connector 112 for connecting to a temperature monitor 114. In the illustrated embodiment, the ECG instrument 110 and the temperature monitor 114, along with a respiration monitor 115, are embodied in unitary fashion by a standard multi-parameter patient monitor 116. The respiration monitor 115 is also (like the ECG instrument 110) operatively connected with the ECG trunk cable 100. In an alternative configuration, individual instruments may be used for monitoring ECG, temperature, or so forth, rather than employing the unitary multi-parameter device 116.

The assembly comprising the feeding tube 70 and the bifurcation 90 is suitably treated as a disposable item that is used one a single patient and then discarded. The electrical adaptor 96 is reusable. The ECG trunk cable 100 and temperature probe cable 102 are also reusable, and in some embodiments are standardized components that may also be used with conventional ECG lead sets or temperature probes, respectively. In an alternative embodiment, the two cables may be replaced by a single cable with two connectors, or by a single cable with a single connector serving both functions.

With continuing reference to FIG. 7 and with further reference to FIGS. 8-10, a suitable construction of the medical device is as follows. The feeding tube 70 is formed, for example by an extrusion process. The formed feeding tube 70 includes the feeding lumen 80 and the electrical lumen 84 parallel with at least a portion of the feeding lumen. The feeding tube 70 is suitably formed of polyurethane, silicone, or another material suitably soft, flexible, corrosion resistant and biocompatible for insertion into the esophagus and stomach. After the extrusion process, access openings 120 are formed into the feeding tube 70 by mechanical drilling, punching, laser cutting, or another suitable process. The access openings 120 are spaced apart along the feeding tube 70, and are located along the feeding tube 70 proximate to the eventual locations of the electrodes. The access openings 120 provide access to the electrical lumen 84. Although not illustrated, it is also contemplated to provide access openings to the electrical lumen 84 for other purposes. For example, optionally a thermal access opening (not illustrated) is similarly formed at the eventual location of the temperature sensor 130. FIG. 8 shows the feeding tube 70 after extrusion and formation of the access openings 120. As extruded, the feeding and electrical lumens 80, 84 extend completely through the distal end 124 of the extruded feeding tube 70, and the distal end 124 typically has relatively sharp or abrupt edges. Preferably, the distal end 124 is processed to plug up or otherwise close off the electrical lumen 84 at the distal end 124, and to smooth edges of the distal end 124 to reduce the likelihood of damage to the esophagus or other contacted tissues during insertion of the feeding tube 70. Some suitable approaches for smoothing the distal end 124 include: mechanical smoothing by grinding, lapping, or so forth; smoothing by thermal reflow using heating by a flame, laser, or other heat source; smoothing by chemical etching; or so forth. Any such processing of the distal end 124 should ensure that the feeding lumen 80 continues to have an opening at the distal end 124 to allow food to pass from the feeding lumen 80 into the stomach—however, this opening at the distal end 124 may optionally be reshaped or otherwise adjusted by the distal end processing.

With reference to FIG. 9, in a separate process the electrical assembly including the set of wires 82 (or, more generally, insulated electrical conductors) and a thermister 130 (or, more generally, a thermister, thermocouple, thermodiode, or other temperature sensor) is assembled. Construction of this assembly includes arranging the wires of the set of wires 82 into a bundle, connecting the temperature sensor 130 with appropriate wires of the set of wires 82, optionally cutting wires to selected lengths, and stripping insulation from wire portions of the wires that are to connect with electrode rings preparatory to making electrical contact with the electrodes. There are eight wires in the illustrative set of wires 82, namely six wires for connecting with the electrode rings 72, 73, 74, 75, 78, 79 and two additional wires for connecting the temperature sensor 130. More or fewer wires can be provided, depending on the number of electrodes, number of temperature sensors (if any), exact electrical requirements of the monitoring instrument, and the number of any additional electrical elements to be connected. For example, in one contemplated variation of the embodiment shown in FIG. 9, the temperature sensor 130 is connected with two wires that also connect with respective electrodes, such that the temperature sensor and the two electrodes share two wires; in this way, the number of wires in the set of wires 82 could be reduced from eight wires to six wires. Moreover, although the wires of the set of wires 82 are illustrated as being straight, the wires of the set of wires may instead be twisted or braided together to enhance the bundling of the wires.

In constructing the electrical assembly, the temperature sensor wires are trimmed to a desired length corresponding to the position of the temperature sensor in the feeding tube, and the temperature sensor 130 is soldered or otherwise connected with the these trimmed wires. The wires that are to connect with electrodes are processed as follows. For each such wire, the insulation is stripped proximate to where the electrode will be connected, so as to form electrically exposed conductor portions in the form of bare wire portions 132 as shown in FIG. 9. (Note that one bare wire portion is not visible in the perspective view of FIG. 9). The bare wire portions 132 are located along the length of the electrical assembly so as to coincide with and be proximate to corresponding access openings 120 when installed in the electrical lumen 84 of the feeding tube 70. Optionally, as shown in FIG. 9 the excess wire length of each wire distal from the bare wire portion 132 is trimmed, and may also be looped, coined, folded back or otherwise modified to facilitate a mechanical interconnection of the electrically exposed conductor with the electrically conductive adhesive portions disposed in the access openings or external electrode portion as will be described. FIG. 9A shows a modified bare wire portion 132a that is modified (as compared with the bare wire portions 132 of FIG. 9) by being looped. In other contemplated embodiments, the bare wire portion is not trimmed; rather, the excess wire length is retained, so that most bare wire portions are located at other than the extreme end of the processed wire.

To form the final multifunction feeding tube shown in FIG. 7, the electrical assembly of FIG. 9 is inserted into the electrical lumen 84 of the feeding tube extrusion of FIG. 8 with the bare wire portions 132 aligned along the feeding tube with corresponding access openings 120.

With continuing reference to FIGS. 7-9 and further reference to FIG. 10 (which illustrates the assembled multifunction feeding tube with the extrusion removed), the electrodes are formed by a process that includes injecting electrically conductive material portions 140 into the access openings 120 of the electrical lumen 84 to electrically contact the proximate bare wire portions 132 of the set of insulated wires 82 disposed in the electrical lumen 84. The electrically conductive material portions 140 are visible only in FIG. 10. In a suitable embodiment, the electrically conductive material portions 140 comprise electrically conductive adhesive portions 140 disposed in the access openings and adhering to the proximate bare wire portions 132. The robustness of this adhesive connection is optionally enhanced by the aforementioned optional looping (e.g., the looped bare wire portion 132a of FIG. 9A), coining, or other modification of the bare wire portions. Optionally, the electrically conductive adhesive portions 140 also adhere to an inner surface of the electrical lumen 84 to assist in retaining the position of the electrical assembly in the electrical lumen 84. In some embodiments the electrically conductive adhesive portions 140 comprises cured electrically conductive polymer material portions, such as, by way of example, cured electrically conductive epoxy portions. In such embodiments, the formation of the electrically conductive adhesive portions 140 includes injecting the material into the access openings 120 to electrically contact the proximate bare wire portions 132, followed by a curing operation that may, by way of illustrative example, include delaying a curing time and optionally applying curing heat by way of an oven or the like. In other contemplated embodiments, the electrically conductive adhesive portions may be made of another material that can be controllably flowed into the access openings 120 and solidified, such as a solder material. Although not illustrated, it is also contemplated to provide additional adhesive portions through additional access openings (features not illustrated), in which the additional adhesive portions may be either electrically conductive or electrically non-conductive, and provide mechanical anchoring of the electrical assembly in the electrical lumen 84.

The electrically conductive material portions 140 extend to be fill the access openings 120, and are flush with or extend slightly beyond the outer surface of the feeding tube extrusion. In some embodiments, these flush or slightly protruding exposed surfaces of the electrically conductive adhesive portions 140 are the accessible electrodes. In other embodiments, an additional electrode element is disposed on the flush or slightly protruding exposed surface of each electrically conductive adhesive portions 140. In the illustrative embodiment, these additional elements are the electrode rings 72, 73, 74, 75, 78, 79, which are annular electrically conductive elements disposed around the outside of the feeding tube and electrically contacting the electrically conductive material portions 140 disposed in the access openings 120. The electrode rings 72, 73, 74, 75, 78, 79 contact the flush or slightly protruding surfaces of the electrically conductive adhesive portions to make electrical contact therewith, and advantageously provide exposed electrode surfaces with radial symmetry. In one suitable embodiment, the electrode rings 72, 73, 74, 75, 78, 79 are made of short cut lengths of stainless steel or platinum tubing.

In other embodiments the additional electrode elements comprise electrically conductive coatings disposed at least over the electrically conductive material portions disposed in the access openings. Optionally, such coatings can extend over the outer surface of the feeding tube extrusion, for example to define annular rings analogous to the illustrated electrode rings 72, 73, 74, 75, 78, 79.

An advantage of including the additional electrode elements (such as the illustrative electrode rings 72, 73, 74, 75, 78, 79, or electrically conductive coatings, or so forth) is that the additional electrode elements can be designed to optimize electrical coupling with the esophagus or other proximate anatomy with which electrical communication is desired. This design may include selection of the material of the additional electrode elements, providing the illustrative electrode rings 72, 73, 74, 75, 78, 79 with sufficient thickness to ensure that they protrude radially outward to make contact with the esophagus wall or other proximate tissue, or so forth. This then allows the electrically conductive adhesive portions 140 to be optimized respective to aspects such as minimizing contact resistance with the bare wire portions 132, optimizing mechanical properties for facilitating the injection and curing, optimizing adhesive qualities, and so forth. Optimization of the electrically conductive adhesive portions 140 may include, for example, selection of material type and amount injected into each access opening 120, control of the injection process mechanics, optimization of the curing process, and so forth.

The electrodes optionally seal the access openings 120 so that the electrical lumen 84 is not exposed to stomach acid or other corrosive biological tissue. The seals can be made in various ways. In some embodiments, the electrically conductive material portions 140 completely fill the access openings 120 so as to seal the access openings 120. Additionally or alternatively, the electrode rings 72, 73, 74, 75, 78, 79 can provide the seal, for example by the mechanism of a tight friction fit to the feeding tube extrusion. Additionally or alternatively, an additional sealant fluid (not shown) may be applied, for example at the periphery of the electrode rings to seal the gap between the electrode ring and the feeding tube extrusion. The seal may be less than perfect, for example permitting some ingress of corrosive fluid into the electrical lumen 84 over a time frame that is statistically longer than the expected useful life of the inserted multi-function feeding tube.

Optionally, and optional thermal access opening (not shown) is also provided, and is suitably filled with a thermally conductive material portion that thermally contacts the temperature sensor 130 and is flush with or protrudes slightly from the external surface of the feeding tube extrusion to define an external thermal contact. The thermally conductive material portion is optionally electrically non-conductive so as to avoid the potential for introducing electrical shunting. As a further option, a thermally conductive ring analogous to the electrode rings 72, 73, 74, 75, 78, 79 may be disposed over the thermal access opening after injection of the optional thermally conductive material portion.

In the electrical assembly of FIG. 9, the electrical conductors comprise the set of wires 82 which are a bundle of discrete insulated wires extending along the electrical lumen 84, and the electrically exposed portions comprise bare wire portions 132 which are formed by stripping the insulation to expose the bare wire portions, and optionally performing further modification such as looping as shown in FIG. 9A.

With reference to FIG. 9B, in an alternative embodiment, the electrical conductors comprise a set of insulated electrically conductive traces disposed on or in a flexible circuit board (i.e., "flex circuit board") 82*b* extending along the electrical lumen 84. In this embodiment, the electrically exposed portions are suitably embodied as exposed portions 132*b* of the electrically conductive traces at which an insulative coating (for example, an oxide, nitride, or oxynitride coating) is removed (or not deposited in the first place) by a suitable photolithographic or other patterning technique. The exposed portions 132*b* are thus similar to bonding pads of circuit boards at which components are conventionally soldered. Optionally, the exposed portions 132*b* are formed on both sides of the flexible circuit board 82*b*, or pass through the flex circuit board 82*b* completely, so that the conductive epoxy is assured of making electrical contact with at least one of the pads. Additionally or alternatively, the flexible circuit board may be twisted to facilitate the electrical contact. In this alternative embodiment, a modified temperature sensor 130*b* may be embodied as a surface mount component that is directly soldered to the elongated insulated flexible circuit board 82*b* at the desired location along the elongated insulated flexible circuit board 82*b*. In a variant embodiment, a socket for the temperature sensor is soldered on the board, and the temperature sensor is mounted via the socket. In yet another alternative embodiment, exposed portions 132*bb* (only one example of which is diagrammatically shown in FIG. 9B) are embodied as tabs that extend away from an edge of the flex circuit board 82*b*. The tabs 132*bb* are suitably pulled through the aligned access openings 120 and wrapped around the outside of the extrusion to provide externally accessible electrodes. The wrapped tabs may be secured by suitable adhesive, which may be electrically conducting or electrically non-conducting.

With reference to FIG. 11, a cross-section of the feeding tube extrusion is shown, revealing the cross-sections of the feeding lumen 80 and the electrical lumen 84. In the illustrated embodiment there is a single feeding lumen and a single electrical lumen. (However, it is also contemplated to include more than one feeding lumen, analogous to the embodiment of FIGS. 1-5, and/or more than one electrical lumen). The electrical assembly (shown in FIG. 9) has a small cross-section sufficient to accommodate the bundle of the set of wires 82 and the temperature sensor 130. Thus, the cross-sectional area of the electrical lumen 84 can be made small and consequently the feeding lumen 80 can be made large. In some embodiments, a ratio of the cross-section of the feeding lumen 80 to the cross-section of the electrical lumen 84 is greater than two. In some embodiments, a ratio of the cross-section of the feeding lumen 80 to the cross-section of the electrical lumen 84 is greater than three. In one embodiment, a ratio of the cross-section of the feeding lumen 80 to the cross-section of the electrical lumen 84 is about four, although even larger ratios are contemplated.

The feeding lumen 80 is preferably a single lumen (as shown), although multiple feeding lumens are also contemplated. A single feeding lumen is less likely to become clogged as compared with a plurality of separate feeding lumens of equivalent cross-sectional area. For rapidity of manufacturing, it is also advantageous for the electrical lumen 84 to be a single lumen (as shown in FIG. 11) and for a single electrical assembly (as shown in FIG. 9) to be constructed and inserted into the single electrical lumen 84. However, the use of multiple electrical lumens with a corresponding multiplicity of electrical assemblies (some or all of which could include a single wire with stripped wire portion) are also contemplated. In the illustrative example of FIG. 11, the electrical lumen 84 has a circular cross-section and is offset from the center of the feeding tube extrusion, and the feeding lumen 80 has a convex outer surface 144 that is approximately parallel with an outer surface of the feeding tube extrusion, and a concave inner surface 146 that is approximately parallel with a portion of the surface of the electrical lumen 84. This configuration is referred to herein as a "smiling Cyclops" configuration (where the electrical lumen 84 is the single "eye" of the Cyclops, and the electrical lumen 80 is the "smiling mouth" of the Cyclops). The smiling Cyclops arrangement provides for a large uninterrupted cross-sectional area for the feeding lumen 80 while retaining a circular cross-section for the electrical lumen 84, and additionally places the feeding lumen 80 proximate to an outer surface of the feeding tube extrusion so as to facilitate formation of the access openings 120. Other cross-sectional configurations are also contemplated.

Another advantage of the embodiments disclosed with reference to FIGS. 7-10 is that the temperature sensor 130 can have various placements along the feeding tube. For example, additional electrodes, such as illustrative electrodes 72, can be located distal from the temperature sensor 130. More generally, the temperature sensor can be located along the feeding tube between electrodes. The temperature sensor wires are thereby shorter, which is advantageous, and the centrally located temperature sensor is less likely to be exposed to corrosive stomach acid which could decrease its longevity. Moreover, by placing the temperature sensor in the esophagus rather than in the stomach more accurate core body temperature measurements are expected to be obtained.

As initially extruded, the feeding tube extrusion has the uniform cross-section shown in FIG. 11 for its entire length, including at its distal end. To protect the electrical assembly from the corrosive esophageal or stomach environment, it is advantageous to seal the distal end of the electrical lumen 84 using a plug, heat sealing, or so forth. Additionally, it is useful to smooth the shape of the distal end by mechanical polishing, grinding, reflow processing, or so forth in order to remove sharp edges.

With reference to FIGS. 12 and 13, an illustrative smoothed distal end 150 is shown, which includes a single reshaped opening 152 that is in fluid communication with the feeding lumen 80, but is not in fluid communication with the electrical lumen 84. The illustrative distal end also includes an auxiliary side opening 154. There are one or more openings near the tip of the tube to permit the food to leave the lumen and enter the stomach of the patient. By way of illustrative example, in one configuration the opening 152 is at the tip (as shown in FIG. 12) and the side opening 154 is perpendicular to the feeding lumen 80 and approximately 5 mm proximal. The side opening 154 allows suctioning of a sample from the stomach even if the primary opening 152 is blocked.

In one suitable approach for forming the tip of FIGS. 12 and 13, a sealing process employs a heated mold that forms the end to the illustrated smoothed shape that is configured for ease of insertion and patient safety and comfort. The feeding tube extrusion advantageously has thin walls for most of its length. Beyond the most distal electrode, however, the electrical lumen 84 is no longer needed and the cross-section is changed from the dual lumen "smiling Cyclops" configuration of FIG. 11 to the single, central, circular lumen 152 shown in FIG. 12. The walls curve inward, allowing the end radius to be maximized for each outside diameter.

Optionally, a radio-opaque marker (not shown) is disposed at the tip of the multifunction feeding tube, for example in the electrical lumen 84 close to the distal end, to enable the tip of the multifunction feeding tube to be viewed with a radiological imaging technique such as x-ray or fluoroscopy. The radio-opaque marker may, for example, be a metallic slug disposed in the electrical lumen 84 close to the distal end.

With reference to FIGS. 6 and 7, the electrodes are spaced apart along the feeding tube with at least one upper or proximal electrode (namely four upper or proximal electrode rings 74, 75, 78, 79, in the illustrative embodiment) disposed above an expected patient heart electrical centerline CL (diagrammatically shown in FIG. 6) and at least one lower or distal electrode (namely two lower electrode rings 72, 73, in the illustrative embodiment) disposed below the expected patient heart electrical centerline CL. This arrangement enables acquisition of electrocardiograph (ECG) signals across the heart.

To accommodate patients of different sizes, the at least one upper or proximal electrode comprises a set of upper or proximal electrodes (namely four upper or proximal electrode rings 74, 75, 78, 79, in the illustrative embodiment) spaced apart along the feeding tube above the expected patient heart electrical centerline CL, the at least one lower or distal electrode comprises a set of lower or distal electrodes (namely two lower or distal electrode rings 72, 73, in the illustrative embodiment) spaced apart along the feeding tube below the expected patient heart electrical centerline. In order to ensure the correct placement of the upper (proximal) and lower (distal) electrodes in the esophagus, a suitable feeding tube placement technique is employed that ensures that the end of the feeding tube is located in the stomach. One suitable approach is the standard ear/nose/xyphoid process method for placement of the distal end in the stomach. Alternatively, a suitable sensor feedback technique can be employed. The feeding tube should be sized so that when properly placed the lower or distal electrodes are in the esophagus, and so that the patient heart electrical centerline CL is between the set of upper (proximal) electrodes and the set of lower (distal) electrodes.

To accommodate variations in patient size or anatomical dimensions, and to accommodate patient growth in neonatal applications, the ECG instrument 110 is configured to selectably operatively connect with a selected one of the set of upper (proximal) electrodes 74, 75, 78, 79 and with a selected one of the set of lower (distal) electrodes 72, 73 via the set of insulated wires 82 disposed in the electrical lumen 84. With reference to FIG. 6, the illustrative electrical adaptor 96 that adapts the wires of the set of wires 82 from the electrode rings into the electrocardiograph (ECG) trunk cable 100 includes a manual switch 160 that enables a nurse, physician, or other qualified person to select the operative upper and lower electrodes from the upper and lower sets of electrodes, respectively, based on a suitable criterion such as patient size. In some embodiments, an electronic or paper chart (not shown) is provided, which lists recommended depth of insertion (naris to stomach) based on spine length, distance from sternum or clavicle to navel, or another suitable externally determinable anatomical dimension. An additional or alternative approach for selecting the selectable upper and lower ECG electrodes is trial-and-error. In the example with four upper electrodes and two lower electrodes, there are eight possible selection combinations, which can be sampled in turn and the combination providing the best ECG trace is then selected.

With reference to FIG. 14, an illustrative switching circuit is shown, which can be implemented using a manual switch such as the switch 160 (see FIG. 6) or automatically using a computer, digital patient monitor (such as the illustrative unitary patient monitor 116 that embodies the ECG, temperature, and respiration monitors 110, 114, 115), or other system having software-based switching capability. In this example, there are six ECG electrodes, i.e. the electrodes 72, 73, 74, 75, 78, 79, that can be switchably connected to simulate the conventional "RA" (right arm), "LA" (left arm), and "LL" (left leg) ECG leads, conventionally used for measuring ECG and respiration. Alternatively, a patient monitor can be designed around the array of esophageal electrodes, with the potential to measure parameters not measureable using only external chest electrodes.

Optionally, as indicated in FIG. 6, the electrodes 72, 73, 74, 75, 78, 79 can also be used to measure respiration. For example, the approach already described with reference to the embodiment of FIGS. 1-5 can be used, in which respiration rate is determined by injecting a low-voltage electrical signal into the patient via a pair of spaced electrodes. The electrical impedance of the connection varies during the act of respiration, so the rate and depth of respiration can be estimated based on the electrical impedance variation. In the case of the array of upper electrodes and the array of lower electrodes, good respiration measurement can be obtained by using the same selected upper and lower electrodes as are used for the ECG measurement. This facilitates, for example, the arrangement of FIG. 6 in which the same ECG trunk 100 suitably feeds both the ECG instrument 100 and the respiration monitor 115.

The embodiments disclosed with reference to FIGS. 6-14 can be manufactured to be "MR conditional" or even "MR safe". The latter designation indicates that a patient having the multifunction feeding tube can safely undergo examination in any magnetic resonance (MR) system; the former designation indicates that a safe diagnosis is possible in some MR systems and/or with under certain specified limitations such as a maximum magnetic field strength. If the multifunction feeding tube is "MR unsafe", it is optionally marked externally to indicate this designation using a metallic coating on plastic parts to supplement the required label icon and enhance the probability that the feeding tube will be removed before an MRI examination.

By way of further illustrative example of embodiments conforming with the examples of FIGS. 6-14, in one suitable embodiment a polyurethane tube is extruded to define the feeding tube extrusion. The size is approximately 1.7 mm outside diameter which corresponds to 5 on the "French" (Fr) scale conventionally used for catheter diameter specification. The two lumens 80, 84 run the length of the extrusion, which is approximately 30 cm in one contemplated embodiment. The electrical lumen 84 has a substantially circular cross-section of about 0.5 mm (0.02 in) diameter. The feeding lumen 80 has a larger cross-section and resembles a crescent in shape, as shown in FIG. 11, and in one embodiment has cross-section area of approximately 0.78 mm$^2$. Advantageously, this 5 Fr multifunction feeding tube has about same feeding lumen area as a conventional (single-function) feeding tube, and, therefore, the flow rate is similar.

At the proximal end, the multifunction feeding tube has the inlet fitting 92 (that is, a "hub") to permit entry of liquid food into the feeding lumen 80. In some embodiments, the inlet fitting 92 is an "enteral-only fitting" rather than a standard Luer-taper fitting. Such an enteral fitting accommodates only those syringes, pumps and adaptors with a mating fitting, so that the feeding tube cannot be inadvertently connected to the patient's vascular system. Optionally, a second hub (not shown) permits administration of oral medications or food supplements without disturbing the primary connection to a pump or reservoir. Both hubs are preferably provided with plugs or caps to prevent backflow and keep the hub clean. The fitting is optionally color-coded orange or amber to help identify its use as a feeding connection.

In one suitable embodiment, the temperature sensing device 130 (or surface-mount or socketed device 130b) disposed inside the electrical lumen 84 is a ceramic thermistor whose electrical resistance decreases as the ambient temperature increases. A suitable location of the thermistor 130 in the subject is in the esophagus, where the lead-length can be relatively short. Placement of the temperature sensor in the stomach is expected to provide less accurate core body temperature measurement due to possible temperature transients during ingestion of food, and may reduce the operational life of the ceramic thermister due to the potential for corrosion from the acid environment inside the stomach. On the other hand, placement of the temperature sensor too high up in the esophagus (that is too proximally in the feeding tube) results in a large number of wires of the set of wires 82 passing alongside the temperature sensor, which can be problematic. Accordingly, in some embodiments a central placement is chosen in which the temperature sensor 130 is between the upper set of electrodes 74, 75, 78, 79 and the lower set of electrodes 72, 73 (as illustrated).

In a suitable embodiment, the dual-lumen 80, 84 feeding tube extrusion (see FIG. 8) is extruded from polyurethane, silicone, or another suitable material. The access openings 120, 122 are suitably made from the outside of the extrusion into the electrical lumen 84 (but not through to the feeding lumen 80) by drilling, punching or so forth in the locations where electrodes are to be provided. The electrical assembly (see FIG. 9) includes the thermistor 130 with its two lead wires. (In some embodiments, it is contemplated to provide two or more temperature sensors, for example with one or more temperature sensors used in respiration measurement as per the thermistors 28, 30 of the embodiment of FIG. 1). The electrical assembly also includes a lead-wire for each electrode to be connected. The insulation of each electrode wire is removed to form the bare wire portions 132, either at the distal end of the wire or at some intermediate point along the wire. The components are then arranged or bundled together to form the electrical assembly with the thermistor and the bare wire portions located in the correct relative positions. During insertion into the electrical lumen 84, the electrical assembly may be held together manually. Additionally or alternatively, the electrical assembly may be held together by an adhesive, a fixture (e.g. ties or so forth), or the like.

The electrical assembly is pulled into the electrical lumen 84 and aligned with the access openings 120. The electrically conductive adhesive portions 140 are injected into the access openings 120 so that these portions are flush with, or slightly protruding from, the tops of the access openings 120. The electrically conductive adhesive defines an electrical path from the appropriate bare wire portion to the outside of the feeding tube extrusion. The electrically conductive adhesive portions 140 optionally also adhere to the inside wall of the electrical lumen 84 to secure the electrical assembly. Optionally, a thermally conductive adhesive portion is injected into the thermal access opening 122 to mechanically secure the thermistor 130 and to provide improved thermal coupling with the exterior of the feeding tube.

The thermistor 130 is suitably a separate component with a cylindrical case and two axial, insulated wire leads on the same side. In an alternative embodiment, the thermistor 130 is fabricated directly on a flexible circuit (which may or may not be an elongated flexible circuit board defining the wires of the set of wires 82), trimmed to meet performance specifications, and encapsulated for electrical insulation.

Additional electrode elements, such as the illustrative electrode rings 72, 73, 74, 75, 78, 79, are optionally added. In one suitable approach, thin coating portions of moderately-conductive paint are applied to the outside of the tube, over the electrically conductive adhesive portions 140. This material can be chosen for properties appropriate to the electrode and for effective bonding to the conductive adhesive portions 140. Alternatively, the electrically conductive adhesive portions 140 can directly define the external electrodes. In this latter case, after injection into the access openings 120, an external roller or other smoothing device is optionally used to spread the material around the outside surface to define an annular external contact surface for each electrode. Alternatively, the additional electrode element (e.g., exterior conductive coating portions) can be applied to the exterior of the feeding tube extrusion before the access openings 120 are punched or otherwise formed.

The multifunction feeding tube embodiments described herein with reference to FIGS. 6-14 are placed and used for feeding in the same way as with a conventional feeding tube. Additionally, ECG waveform, heart rate, and, optionally, impedance respiration rate are obtained by connecting the electrical adaptor 96 to the conventional ECG trunk cable 100 the same way as an array of surface electrodes are conventionally connected. Advantageously, the same upper and lower electrodes across the patient heart electrical centerline CL can be used for both ECG and respiration measurements. An advantage of the disclosed multifunction feeding tube is that the nurse, physician or other medical personnel do not need to connect electrodes for ECG to their respective "correct" locations (e.g., right-arm electrode to the RA channel, left leg to the LL channel, et cetera). When using the ECG capability of the multifunction feeding tube, the standard labels on the monitor (e.g. "Lead II") do not apply, the waveforms may not precisely replicate those of a conventional ECG. However, the heart rate and respiration rate are accurately measured. In similar fashion, by connecting the electrical adaptor 96 to the temperature probe cable 102, core body temperature is monitored continuously from the esophagus.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A device comprising:
    a feeding tube including a feeding lumen with an opening at a distal end of the feeding tube and an electrical lumen having access openings spaced apart along the feeding tube;
    a set of insulated electrical conductors disposed in the electrical lumen, the set of insulated electrical conductors having electrically exposed portions proximate to the access openings; and
    electrodes comprising:
        (i) electrically conductive material portions disposed in the access openings and electrically contacting the proximate electrically exposed portions of the set of insulated electrical conductors disposed in the electrical lumen, and
        (ii) annular electrically conductive coatings disposed around the outside of the feeding tube and electrically contacting the electrically conductive material portions disposed in the access openings, the electrically conductive coatings being disposed over the electrically conductive material portions disposed in the access openings and over a proximate annular portion of the outside of the feeding tube, the annular electrically conductive coatings being made of a different material from the electrically conductive material portions.

2. The device as set forth in claim 1, wherein the electrically conductive material portions comprise electrically conductive adhesive portions disposed in the access openings and adhering to the proximate electrically exposed portions.

3. The device as set forth in claim 2, wherein the electrically conductive adhesive portions also adhere to the electrical lumen.

4. The device as set forth in claim 2, wherein the electrically conductive adhesive portions comprise electrically conductive polymer material portions.

5. The device as set forth in claim 4, wherein the cured electrically conductive polymer material portions comprise electrically conductive epoxy portions.

6. The device as set forth in claim 1, wherein the electrodes seal the access openings.

7. The device as set forth in claim 1, wherein the feeding tube is sized and the electrodes are placed such that at least one lower or distal electrode is disposed in the esophagus, at least one upper or proximal electrode is disposed in the esophagus, and an expected patient heart electrical centerline is disposed between the at least one lower or distal electrode and the at least one upper or proximal electrode.

8. The device as set forth in claim 7, wherein:
the at least one upper or proximal electrode comprises a set of upper or proximal electrodes,
the at least one lower or distal electrode comprises a set of lower or distal electrodes, and
the device is configured to selectably operatively connect a selected one of the set of upper ECG electrodes and a selected one of the set of lower ECG electrodes with an ECG instrument via the set of insulated electrical conductors disposed in the electrical lumen.

9. The device as set forth in claim 8, further comprising one of:
a manual switch providing said configuration for selective operative connection, and
an electrocardiograph instrument or patient monitor electronically providing said configuration for selective operative connection.

10. The device as set forth in claim 7, further comprising:
a temperature sensor disposed in the electrical lumen along the feeding tube between the at least one lower or distal electrode and the at least one upper or proximal electrode, the temperature sensor being operatively connected with the set of insulated electrical conductors disposed in the electrical lumen.

11. The device as set forth in claim 1, wherein the set of insulated electrical conductors disposed in the electrical lumen comprises electrically conductive traces of a flexible circuit board, and the electrically exposed portions comprise exposed portions of the electrically conductive traces.

12. The device as set forth in claim 11, wherein the exposed portions of the electrically conductive traces are on both sides of the flexible circuit board.

13. The device as set forth in claim 11, further comprising a temperature sensor electrically connected to the flexible circuit board by surface mounting or socket mounting or other standard means of direct electrical interconnection such as soldering.

14. The device as set forth in claim 1, wherein the feeding tube comprises a polyurethane feeding tube or a silicone feeding tube.

15. The device as set forth in claim 1, wherein the feeding lumen comprises a single feeding lumen and the electrical lumen comprises a single electrical lumen.

16. The device as set forth in claim 1, wherein the device is MR unsafe and is marked externally to indicate this designation using a metallic coating on the feeding tube.

17. A device comprising:
a feeding tube including a feeding lumen with an opening at a distal end of the feeding tube and a single electrical lumen having access openings spaced apart along the feeding tube;
a set of insulated electrical wires disposed in the single electrical lumen, the set of wires having electrically exposed bare wire portions proximate to the access openings of the single electrical lumen; and
electrodes comprising electrically conductive material portions disposed in the access openings of the single electrical lumen and electrically contacting the proximate electrically exposed bare wire portions of the set of insulated electrical wires disposed in the single electrical lumen.

18. The device as set forth in claim 17, wherein the bare wire portions included looped bare wire portions.

19. The device of claim 17 wherein the electrodes include a set of upper or proximal electrodes and a set of lower or distal electrodes, and the device further comprises:
a switch configured to operatively connect one electrode of the set of upper or proximal electrodes and one electrode of the set of lower or distal electrodes to an electrocardiograph (ECG) instrument.

20. The device as set forth in claim 19, wherein the feeding tube is sized and the electrodes are placed respective to a patient such that the set of upper or proximal electrodes are disposed in an esophagus, the set of lower or distal electrodes are disposed in an esophagus, and an expected patient heart electrical centerline is disposed between the operatively connected one electrode of the set of upper or proximal electrodes and operatively connected one electrode of the set of lower or distal electrodes.

21. The device as set forth in claim 19, wherein the feeding tube is sized and the electrodes are placed respective to a patient such that the set of upper or proximal electrodes are disposed in an esophagus, the set of lower or distal electrodes are disposed in an esophagus, and an expected patient heart electrical centerline is disposed between the operatively connected one electrode of the set of upper or proximal electrodes and operatively connected one electrode of the set of lower or distal electrodes while the distal end of the feeding tube is in the stomach.

22. The device as set forth in claim 19, further comprising:
said ECG instrument; and
a respiration monitor, the switch further configured to operatively connect the same one electrode of the set of upper or proximal electrodes and the same one electrode of the set of lower or distal electrodes to the respiration monitor.

23. The device as set forth in claim 19, wherein the switch is selected from a group consisting of:
a manual switch providing said configuration for selective operative connection, and
an electrocardiograph instrument or patient monitor electronically providing said configuration for selective operative connection.

24. A method of constructing a device, the method comprising:
forming a feeding tube including a feeding lumen and an electrical lumen, the electrical lumen having access openings spaced apart along the feeding tube;
forming a set of insulated electrical conductors by stripping insulation to form electrically exposed portions;
after forming the feeding tube with the access openings and after forming the set of insulated electrical conductors with electrically exposed portions, inserting the set of insulated electrical conductors with electrically exposed portions into the electrical lumen of the feeding tube with the electrically exposed portions proximate to the access openings after the inserting;
after the inserting, forming electrodes by a process including:
injecting electrically conductive material portions into the access openings of the electrical lumen to electrically contact the proximate electrically exposed portions of the set of insulated electrical conductors disposed in the electrical lumen, and
after the injecting, disposing outer electrode elements or coating portions over at least the electrically conductive material portions so as to define exterior surfaces of the electrodes.

25. A medical device constructed by a method set forth in claim 24.

* * * * *